(12) United States Patent
Lebet

(10) Patent No.: US 7,470,274 B2
(45) Date of Patent: Dec. 30, 2008

(54) SINGLE-BLOW SHOCKWAVE GENERATION DEVICE

(75) Inventor: Alain Lebet, Lausanne (CH)

(73) Assignee: LMA Urology LImited, Mahe (SC)

( * ) Notice: Subject to any disclaimer, the term of this patent is extended or adjusted under 35 U.S.C. 154(b) by 320 days.

(21) Appl. No.: 10/545,107

(22) PCT Filed: Jan. 30, 2004

(86) PCT No.: PCT/FR2004/000208

§ 371 (c)(1),
(2), (4) Date: Aug. 10, 2005

(87) PCT Pub. No.: WO2004/078048

PCT Pub. Date: Sep. 16, 2004

(65) Prior Publication Data

US 2006/0069395 A1    Mar. 30, 2006

(30) Foreign Application Priority Data

Feb. 14, 2003 (FR) .................................. 03 01793

(51) Int. Cl.
*A61B 17/22* (2006.01)
(52) U.S. Cl. .................. 606/128; 606/2.5; 606/127
(58) Field of Classification Search ......... 606/127–128, 606/2.5; 601/4; 124/56–77, 26–29; 173/93.7
See application file for complete search history.

(56) References Cited

U.S. PATENT DOCUMENTS

| | | | |
|---|---|---|---|
| 3,250,334 A * | 5/1966 | Sussman | ...................... 173/18 |
| 4,016,873 A | 4/1977 | Anderson | |
| 4,716,890 A | 1/1988 | Bichel | |
| 5,160,336 A | 11/1992 | Favre | |
| 5,449,363 A * | 9/1995 | Brust et al. | .................. 606/128 |
| 5,613,483 A * | 3/1997 | Lukas et al. | .................. 124/73 |
| 5,906,623 A | 5/1999 | Peterson | |
| 2002/0010486 A1 | 1/2002 | Hirt | |

FOREIGN PATENT DOCUMENTS

| | | |
|---|---|---|
| EP | 0317507 | 5/1989 |
| EP | 1163882 | 12/2001 |
| WO | 95/22934 | 8/1995 |
| WO | 98/26705 | 6/1998 |

* cited by examiner

*Primary Examiner*—Eric F Winakur
*Assistant Examiner*—Michael T. Rozanski
(74) *Attorney, Agent, or Firm*—Ostrager Chong Flaherty & Broitman P.C.

(57) ABSTRACT

The invention relates to a single-blow mechanical shockwave generation device used in urological surgery for disintegration of urinary duct stones, comprising a striking device which strikes a shock wave generation device at high speed. The shock waves are transmitted by a shock wave transfer device to an object for destruction with which the shock wave transfer device is in direct or indirect contact. The striking device is displaced by way of the expansion of a high-pressure gas introduced prior to each shock wave generation into an accumulation device. The accumulation device is supplied with high pressure gas from independent gas stores and with supply and sealing devices. The stored gas is released by the manual manipulation of a control device which connects the accumulation device to the striking device.

18 Claims, 5 Drawing Sheets

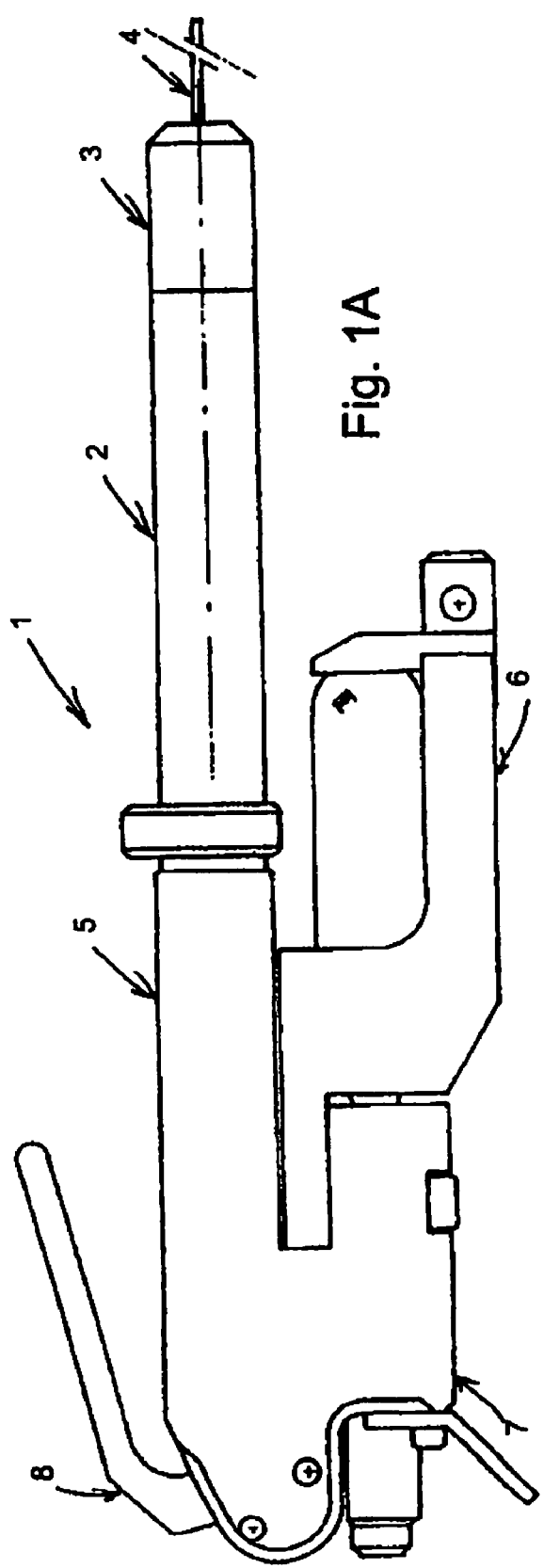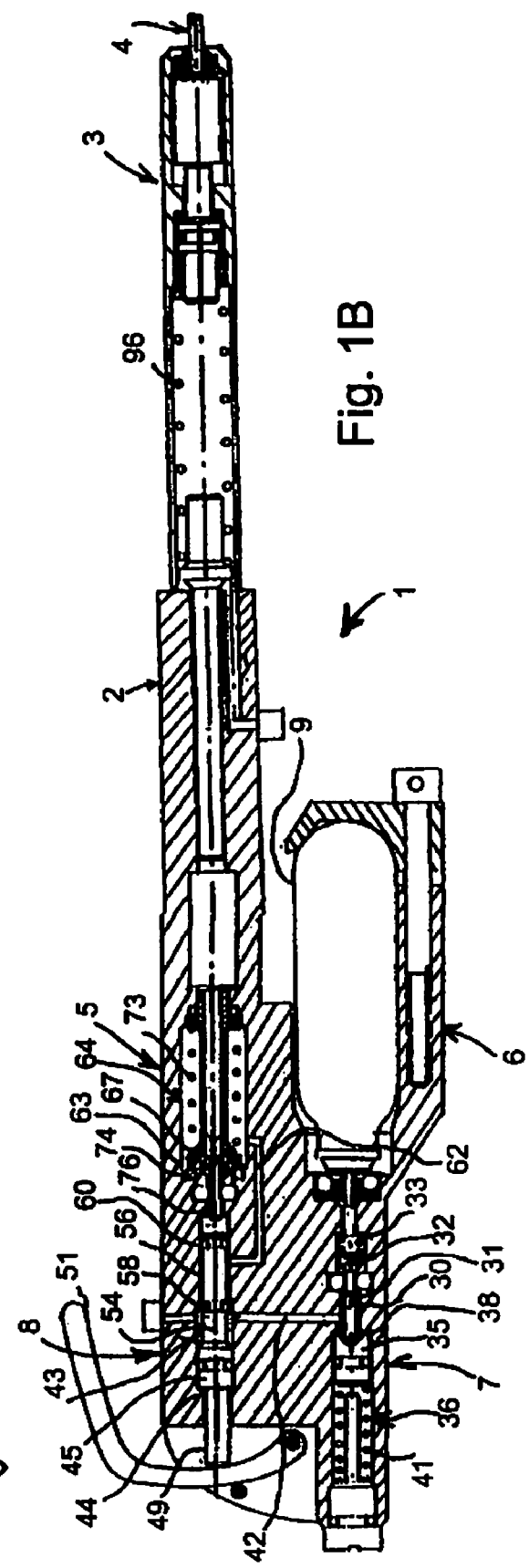

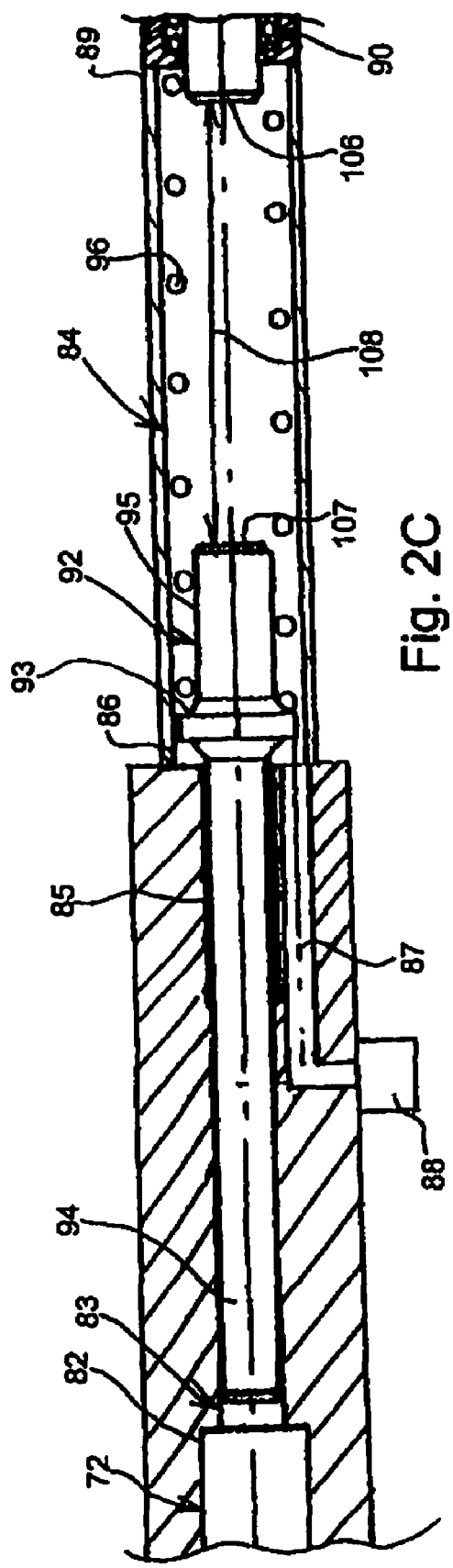
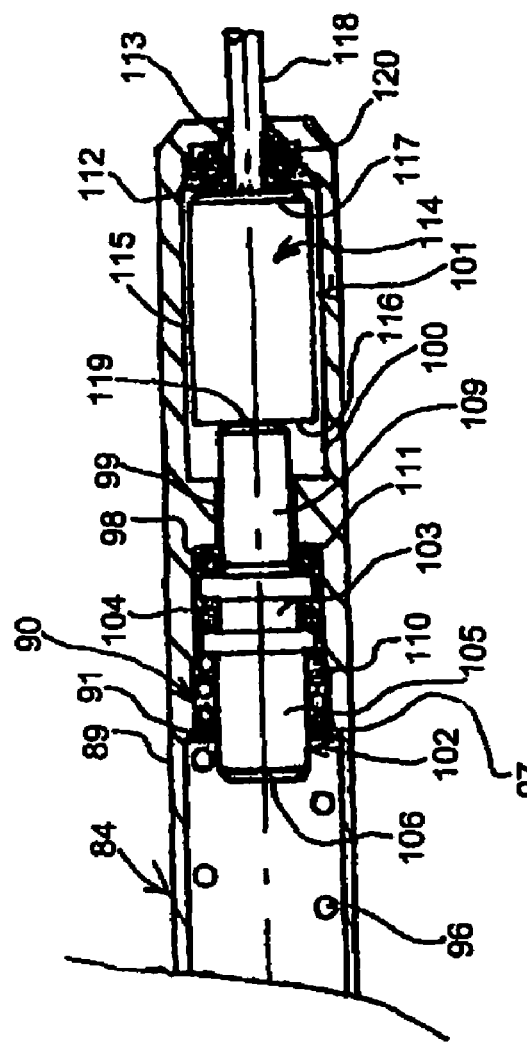
Fig. 2C
Fig. 2D

SINGLE-BLOW SHOCKWAVE GENERATION DEVICE

CROSS-REFERENCE TO RELATED APPLICATION

The present application is a U.S. National Stage entry of International Patent Application No. PCT/FR2004/000208 filed Jan. 30, 2004, and claims priority under 35 U.S.C § 119 of French Patent Application No. 03/01793 filed Feb. 14, 2003.

BACKGROUND OF THE INVENTION

The invention refers to a single-blow shockwave generation device and its implementation process.

Shockwave generation devices are notably used in urological surgery for disintegration of urinary duct stones. The prior art includes two main types of shockwave generation devices: a first type concerning extra-corporeal shockwave generation devices, and a second type concerning percutaneous shockwave generation devices.

Disintegration devices of the first type use an electrical or piezo-electrical shockwave generator where the shockwave guide is comprised of a pocket containing a fluid, in contact with patient's body cooperating with an ellipsoidal reflector which receives a shockwave diffused into a wide space, to focus it through a widely open cone whose apex is located inside the urinary stone to be disintegrated, so that the shockwave is of low amplitude when it crosses through living tissues in order to reduce lesions to said tissues to the minimum possible extent, and of maximum amplitude when concentrated at cone apex.

Disintegration devices of the second type use, for example, specialized endoscopes to match the nature of the intervention to be performed, depending on the size and position of the urinary stone to be evacuated. When the stone is inside the kidney, the endoscope is introduced percutaneously directly into the kidney. When the stone is in the ureter, it is advisable to introduce the endoscope by natural paths via the bladder and up into the ureter. The shockwave is transmitted by a waveguide, which is a metallic rod of circular cross-section, of a diameter of ten to twenty tenths of a millimeter, and able to tolerate elastic deformation. The shockwave guide features a first end where the shockwave is generated and a second end which is applied against the stone.

Disintegration devices of the first type do not allow high amplitude shockwave production, due to risk of lesions to living tissues crossed through. Consequently, stone disintegration requires multiple shocks which reduce the stone into small fragments which can be evacuated through the urinary ducts.

Disintegration devices of the second type, notably that described in European patent EP0317507, use low amplitude shockwave trains whose characteristic feature is also to break the stone to be disintegrated into multiple fragments which can be eliminated by suction, washing, or evacuation through natural paths.

Disintegrated stone fragment elimination through natural paths is very painful, which makes elimination by washing preferable whenever possible, further to an intervention by endoscopy. These stone elimination modes feature a drawback, in that there always remains uneliminated stone debris which can act as a basis for new stone formation.

Gas sealing devices between moving parts in these devices generally include O-rings, for which sealing is obtained by cooperation, either between the higher and lower sealing circles of the O-rings pressed between two flat surfaces or through cooperation between an inner lateral sealing circle and an outer lateral sealing circle of the O-ring pressed between a revolution bore and a revolution cylinder. These sealing devices can be classified, for example, into three types of devices: a sealing device of the first type is comprised of an O-ring positioned in a groove machined in a bore and whose sealing is ensured by cooperation between the inner lateral sealing circle and the outer lateral sealing circle. A sealing device of the second type is comprised of an O-ring located in a groove machined in a revolution cylinder. A sealing device of the third type is comprised of an O-ring located in a circular groove undercut in a flat surface.

SUMMARY OF THE INVENTION

The present invention relates to a wave generation device, generating a high amplitude wave transmitted either percutaneously or naturally, via an endoscope, permitting controlled fragmentation of the urinary stone in order to break it into a small number of fragments of the necessary and sufficient size to allow their manual extraction by way of tweezers through the endoscope which was implemented in order to visualize, seize and extract them.

BRIEF DESCRIPTION OF THE DRAWINGS

The following description of the invention will be better understood by reference to the appended illustrations, in which:

FIG. 1A shows a vertical view of a device according to the preferred 30 embodiment of the invention.

FIG. 1B shows a schematic cross-section of the device according to the preferred embodiment of the invention, in operating condition.

FIGS. 2A to 2D each show a detail of FIG. 1B, the whole of these figures corresponding to the entirety of FIG. 1B.

DETAILED DESCRIPTION OF THE PRESENT INVENTION

Figures 1C, 1D:
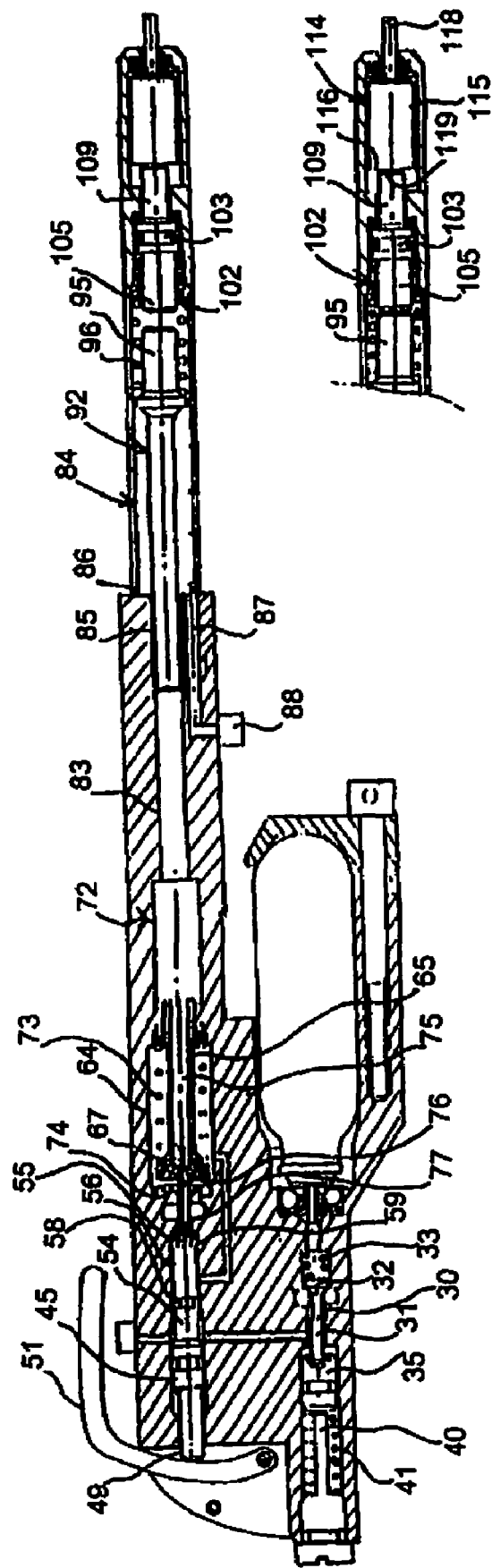
FIG. 1C shows a schematic cross-section of FIG. 1A after initiation of an operating cycle.
FIG. 1D shows a detail of FIG. 1C at the time of shockwave generation.

The invention consists of a single-blow mechanical shockwave generation device (FIG. 1A and FIG. 1B) including striking device 2 which strikes, at high speed, generation device which generate a shockwave 3. The shockwave is transferred through shockwave transfer device 4 to an object to be disintegrated, with which said transfer device is put into direct or indirect contact. Striking device 2 is put into motion by the expansion of a high pressure gas introduced, prior to each shockwave generation, into accumulation device 5 supplied with high pressure gas, from independent very high pressure gas stores 6, by way of gas expansion device 7 and of supply and sealing devices. The gas stored in accumulation device 5 is released by manual operating of control device 8 which renders gastight, through a sealing device, the intercommunication between stores 6 and expansion device 7, on the one hand, and with accumulation device 5, on the other. Manual operating of the control device 8 establishes intercommunication between accumulation device 5 and striking device 2. Return to the initial condition of striking device 2 is ensured by the release of the accumulated energy, by mechanical device, during the shockwave production cycle. Return to initial condition of control device 8 is ensured by the action of high pressure gases which remained at expansion device 7 and by the corresponding supply device.

The gas used can be assimilated to a perfect gas at operating temperature, which is approximately twenty degree Celsius, in an accumulation chamber, making up an accumulation device, and at operating pressure which is a high pressure of approximately fifteen to thirty bar, and chemically compatible with its intended utilization. For example, the gas can be air or nitrogen from a gas cylinder pressurized at a very high pressure of approximately two hundred bar, making up an independent gas store whose content can vary from half a liter to a few liters. It is connected to the single-blow mechanical shockwave generation device 1 via a flexible hose and through a pressure-relief valve. The hose and valve make up a pressure-relief device that is secured to the gas cylinder and which reduces the very high pressure from two hundred bar to a high pressure of fifteen to thirty bar.

Figure 2A:
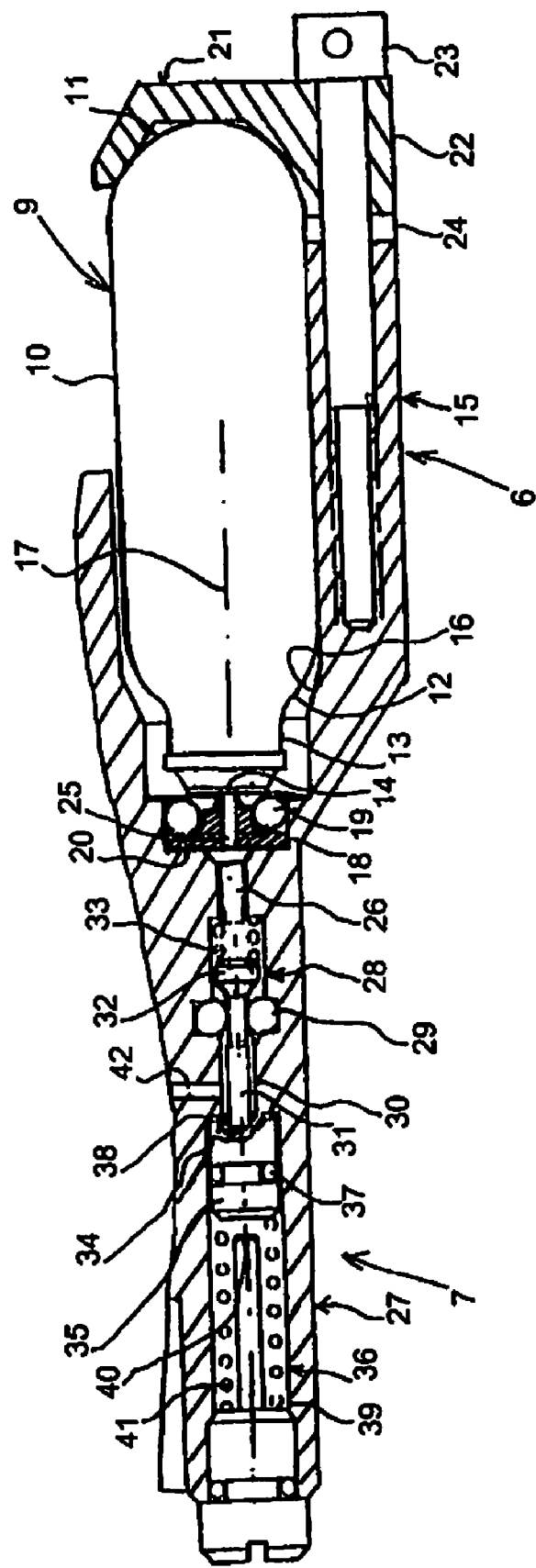

In a preferred embodiment of the invention, the gas used is, for example, carbonic gas commercially available in a single-use gas micro-container 9 (FIG. 2A), making up a gas store of a content of approximately two centiliters at a pressure of approximately seventy bar, in which the carbonic gas is liquid, permitting storage of a significant carbonic gas volume in a small store. Carbonic gas is also known as carbon dioxide gas. The description hereinafter can also apply to other gases whereas remaining within the scope of the invention.

The gas micro-container 9 is comprised of a cylindrical body 10 whose outer diameter is approximately eighteen millimeters, and whose rear end 11 is closed by a hemispherical wall and front end 12 is extended by a stepped section, then by a neck 13 comprising a lateral part, essentially cylindrical, closed by a closing capsule 14. The stepped section and neck 13 assembly features a length of approximately thirteen millimeters and the total length of the assembly is approximately eighty millimeters. Gas micro-container 9 is directly integrated into single-blow mechanical shockwave generation device 1. It is housed into cradle 15 comprised of two half-cradles. Front half-cradle 16 is comprised of a revolution-cylindrical bore, along first symmetry axis 17, of a diameter slightly larger than that of gas micro-container body 9, and features a bottom section fitted with calibrated receptacle 18 which accommodates neck 13 of gas micro-container 9. The lateral part is equipped with a first sealing device of first type 19, with respect to the lateral part of neck 13, whereas the central part of calibrated receptacle 18 features a perforation device 20 which pierces closing capsule 14. Rear half-cradle 21 is comprised of holding device 22 for the hemispherical bottom section of gas micro-container 9, centered on the first symmetry axis 17, and capable of sliding, parallel to the latter, thanks to guide stir-up 24 and clamping device 23 which bears upon front half-cradle 16. The guide stir-up features wide lateral openings which allow sliding of front end 12 of gas micro-container 9 into calibrated receptacle 18 of front half-cradle 16, when the rear half-cradle 21 is retracted. It is only necessary to slide holding device 22 which comes against stop upon hemispherical bottom section 11, then to tighten by pushing gas micro-container 9 against perforation device 20 until closing capsule 14 is pierced. Perforation device 20 features a gas transfer device. Perforation device 20 is, for example, of the type used on single-use butane gas cylinders, and a gas transfer device is a central cylindrical bore 25 allowing circulation of the gas from micro-container 9. Perforation device 20 is intercommunicated, through a first duct 26, with pressure-relief device 27, integrated with single-blow mechanical shock with generation device 1, making up a gas pressure-relief device 7 (FIG. 1A and FIG. 1B). It is comprised, for example, of a first cylinder revolution chamber 28 (FIG. 2A) in the rear section, from which first duct 26 is routed, and whose front section includes a first circular aperture edged by a second sealing device of the first type 29. The first circular aperture extends into a second duct 30 in which, to permit gas passage, valve shank 31 of a gas supply valve slides freely, said valve featuring a valve head 32 located in first chamber 28, and of a diameter significantly smaller than that of first chamber 28, whose lower section features an annular sealing surface which surrounds valve shank 31. The upper part of valve head 32 is pushed back by a first calibrated spring 33 in order to press the annular sealing surface of valve head 32 onto the second sealing device of the first type 29. The free end of valve shank 31 slides through a first bore 34, of a defined depth, acting as a guide, and machined in the head of a first cylindrical piston 35, whose bottom, of first bore 34, acts as a pusher, pushing back valve shank 31. The first piston 35 slides through second revolution-cylindrical chamber 36 which it divides into a first and a second space, of variable volume, sealed from each other by way of a first sealing device of the second type, solid with first piston 35. Second duct 30 leads into the rear section 38 of second chamber 36, partly separating the first space of second chamber 36, through a second circular aperture allowing free sliding of valve shank 31 and intercommunicating second chamber 36 with the gas circuit. Rear section 38 of second chamber 36 acts as a mechanical stop for the head of first piston 35. The second space, partly separated by front section 39 of second chamber 36, includes a piston stop 40, coaxial with that of second chamber 35, thereby limiting the stroke of first piston 35 and acting as a guide for a second calibrated spring 41.

The assembly comprised by first and second chambers 28 and 36, the gas supply valve, first piston 35, first and second calibrated springs 33 and 41, makes up a gas pressure-relief device 7 (FIG. 1A and FIG. 1B) allowing a nominal pressure, defined with a good accuracy comprised between fifteen and thirty bar, to be established in the second gas duct 30 (FIG. 2A) which surrounds valve shank 31.

Figure 2B:
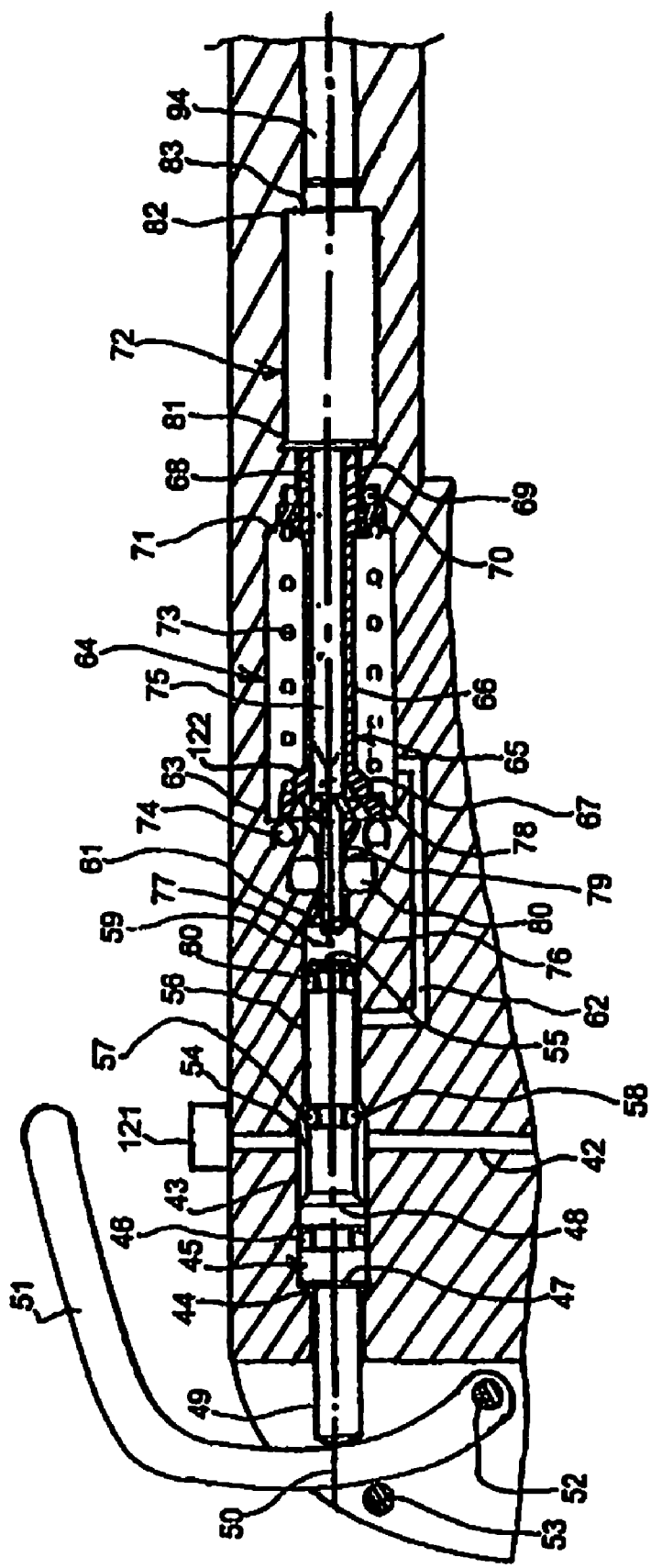

A third duct 42 (FIG. 2B), coming out from second duct 30, leads through the lateral wall to a third revolution-cylindrical chamber 43. The third chamber includes a rear section 44 in which a second piston 45 slides. This piston comprises a second gas sealing device of the second type 46, a rear section 47 and a front section 48. The bottom of rear section 44 in third chamber 43 features a circular aperture through which a first cylindrical pusher 49 passes freely, said pusher 49 being solid with rear section 47 of the second piston 45 and preferably oriented coaxially with the second revolution symmetry axis 50 of third chamber 43, which is actuated by manual operating device of control device 8 (FIG. 1A and FIG. 1B). The manual operating device for first pusher 49 preferably consist of pushing-in second piston 45 into third chamber 43. A manual device is, for example, comprised of a lever 51 hinged around a rotation axis 52, perpendicular and offset with respect to the revolution symmetry axis 50 of third chamber 43, and comprising a symmetry plane which contains revolution symmetry axis 50, and perpendicular to rotation axis 52. The motions of hinged lever 51 are limited by a stop 53. The front section 48 of second piston 45 features a revolution-cylindrical control rod 54, with a captive end on front side 48 of first piston 45 and a free end 55 freely passing through a fourth revolution cylindrical duct 56, and coaxial with the revolution symmetry axis 50 of third chamber 43. The fourth duct 56 leading from the bottom of the front section 57 of third chamber 43 is edged by a coaxial tapered revolution surface which acts as a guide for a third sealing device of the second type 58. The sealing device 58, which is neutralized, allows gas flow into the fourth duct 56 when second piston 45 is bearing against the bottom of the rear section 44 of third chamber 43. But when first pusher 49 is actuated by hinged lever 51, sealing device 58 penetrates into fourth duct 56 and ensures gas sealing of the front section 57 of third chamber 43. Control rod 54 extends and its free end 55 penetrates into a second bore 59, solid with the body of third chamber 43. The free end 55 of control rod 54, internal to second bore 59, includes a fourth sealing device of the second type 60. The stroke of second piston 45 is limited at rear position by the mechanical stop of its rear section 47 on the bottom of the rear section 44 of third chamber 43, and is limited in front position by the mechanical stop of free end 55 of control rod 54 on the bottom 61 of second bore 59. In the front position of second piston 45, the third sealing device of the second type 58 blanks off the fourth duct 56.

A fifth duct 62 (FIG. 2B) includes an inlet aperture leading into the fourth duct 56, downstream of the position of the fourth sealing device of the second type 58, as well as an outlet aperture leading into the rear section of a fourth chamber 64, which is a high pressure gas accumulation device, preferably revolution-cylindrical on a symmetry axis which is merged with that of second stage 59. This fourth chamber includes a discharge valve 65. The valve is comprised of a valve body 66, which is tubular, revolution-cylindrical, and coaxial with that of fourth chamber 64, and of a diameter of approximately one third of that of fourth chamber 64. The valve includes a valve head 67, featuring a flat rear section and a tapered revolution front section 122, of a diameter practically double of that of the valve body on which it connects. The valve includes a valve body base 68 which slides through a third bore 69, of a diameter the same order of magnitude as that valve body 66, featuring a third sealing device of the first type 70 which cooperates with valve body base 68. The third bore 69 is machined in the bottom above front section 71 of the fourth chamber 64, and leads into a fifth chamber 72 which is an expansion chamber. The rear face of valve head 67 is kept pressed against the bottom of rear section 63 of fourth chamber 64 by a first helical spring 73 which bears on the bottom of front section 71 of fourth chamber 64. The rear face of valve head 67, which is circular, features an annular sealing zone next to its edge, which cooperates with a first sealing device of the third type 74, solid with the bottom of rear section 63 of fourth chamber 64. The tubular internal space of valve 66 makes up a sixth duct 75 whose inlet aperture, at the rear face of valve head 67, is flared and essentially tapered. The central section of valve head 67 features a second cylindrical pusher 76, coaxial with second bore 59, comprising a free end 77 and a captive end connected to the rear side of valve head 67 by spacers 78, integrated in the flared aperture of sixth duct 75, and sliding in a fourth revolution bore 79 which interconnects the bottom of rear section 63 of fourth chamber 64 with the bottom of second bore 59. A fourth sealing device of the first type 80, solid with fourth bore 79, ensures sealing between second bore 59 and sixth duct 75. Second pusher 76 features a diameter significantly smaller than that of second bore 59, and a total length which is such that, when valve head 67 cooperates with the first sealing device of the third type 74 to isolate the sixth duct 75 from fourth chamber 64, the free end 77 of second pusher 76 leads into the bottom of second bore 59.

When second piston 45 is in the front position, the free end 55 of control rod 54 presses against the free end 77 of second pusher 76 and thereby pushes back valve head 67 and separates it from the bottom of rear section 63 of fourth chamber 64, by compressing the first helical spring 73, therefore releasing the opening of sixth duct 75. The fourth chamber 64 is intercommunicated through sixth duct 75 with fifth chamber 72. The fifth chamber 72 is of revolution-cylindrical shape, with a rear section 81, in which sixth duct 75 opens, and a front section 82 from which a fifth revolution-cylindrical bore 83 begins. The fifth bore 83 is preferably coaxial with the symmetry axis of fifth chamber 72. Fifth chamber 72 features a diameter slightly larger than that of valve body base 68, and a significantly smaller length. Fifth bore 83 (FIG. 2C) leads into a sixth cylindrical rotation chamber 84, which is coaxial with fifth bore 83, of a diameter essentially equal to that of valve body base 68 and a length essentially double of that of fourth chamber 64. Fifth bore 83 features a decompression zone 85 of a slightly larger diameter, leading into sixth chamber 84, and of a length essentially equal to one third of the length of fifth bore 83. Sixth chamber 84 features a rear section 86 in which fifth bore 83 leads, and from which at least one seventh duct 87 begins. The duct 87 is open to the atmosphere either directly, or via a check valve 88. Sixth chamber 84 comprises a front section 89 in whose bottom a seventh revolution-cylindrical chamber leads, coaxial with sixth chamber 90 (FIG. 2C and FIG. 2D), intercommunicated with sixth chamber 84 via a sixth revolution-cylindrical bore 91, of a diameter significantly larger than that of fifth bore 83, and smaller than that of sixth chamber 90. Fifth bore 83 (FIG. 2C) acts as guide and drive device for a striking hammer 92, making up a striking device. Striking hammer 92 is comprised of hammer body 93, of low thickness, and of a diameter slightly smaller than that of the sixth chamber in which it is located, featuring a rear face directed towards the rear section 86 of sixth chamber 84, and a front face, directed towards the front section 89 of sixth chamber 84. A third, revolution-cylindrical piston 94, coaxial with fifth bore 83 is solid with the rear face of hammer body 93, and slides through fifth bore 83. Third piston 94 features a diameter slightly smaller than that of fifth bore 83, in order to obtain sufficient sealing to permit its propulsion by gases. A revolution-cylindrical striking head 95, coaxial with third piston 94, is secured to the front face of hammer body 93. Striking head 95 is of a diameter significantly larger than that of third piston 94, and a length of approximately one quarter of the length of third piston 94. A second helical spring 96 which bears on front section 89 of sixth chamber 84, and on hammer body 93, presses the hammer body onto the bottom of rear section 86 of sixth chamber 84, therefore keeping third piston 94 depressed in fifth bore 83.

Seventh chamber 90 (FIG. 2D) includes a rear section 97 intercommunicating with sixth chamber 84 through sixth bore 91, and a front section 98 whose bottom features a seventh revolution-cylindrical bore 99 coaxial with seventh chamber 90, and of a diameter essentially equal to fifth bore 83, thereby allowing seventh chamber 90 to intercommunicate with the rear section 100 of eighth chamber 101. Seventh chamber 90 contains a shockwave generating interface device 102 comprised of a revolution-cylindrical interface device body 103, capable of sliding in seventh chamber 90, and comprising a fifth sealing device of the second type 104, which isolates front section 98 of the seventh chamber from rear section 97. The interface device body 103 features a rear face directed towards rear section 97 of seventh chamber 90, and a front face directed towards front section 98 of seventh chamber 90. The rear face of interface device body 103 comprises a strike anvil 105, of the same diameter as striking head 95, whose length, when cumulated with that of interface device body 103, is essentially equal to the length of striking head 95 cumulated with that of hammer body 93. The length of sixth bore 91 is determined so that the free end 106 of strike anvil 105 protrudes from the bottom of front section 89 of sixth chamber 84, and that distance 108 (FIG. 2C) which separates free end 106 of strike anvil 105 from free end 107 of striking head 95 is of the same order of magnitude as the length of third piston 94 when reduced by a sufficient amount to ensure, in fifth bore 83, a residual guidance effect for third piston 94 at end of travel. The front face of interface device body 103 features a first shockwave transfer device 109, revolution-cylindrical and coaxial with seventh chamber 90, and of a diameter essentially equal to that of third piston 94 and a length essentially equal to that of strike anvil 105. The length of seventh bore 99 must be sufficient to ensure correct guidance of shockwave generation interface device 102; however, it must allow protrusion of first shockwave transfer device 109 in the bottom of rear section 106 of eighth chamber 101. A third helical spring 110 bearing, on the one hand, on the bottom of rear section 97 of seventh chamber 90 and, on the other, on the rear section of interface device body 103, presses the latter onto a first toroidal damping device 111 bearing, on the one hand, on the edge of front section of interface device body 103 and surrounding the first shockwave transfer device 109, and, on the other, on the bottom of front 98 of seventh chamber 90. The front section 112 of eighth chamber 101 comprises an eighth bore 113, revolution cylindrical, coaxial with eighth chamber 101, and of a small diameter, of approximately one half of the diameter of third piston 94 which intercommunicates with the outside.

Eighth chamber 101 contains a shockwave guide head 115 of a second shockwave guide device 114, revolution-cylindrical, of a diameter slightly smaller than that of eighth chamber 101, whose rear face 116 is flat-shaped and whose front face 117 is essentially flat-shaped and comprises, squarely secured at its centre, a shockwave guide rod 118 which passes through eighth bore 113 and which acts as guide for shockwave guide head 115 of the second shockwave guide device 114. When the single-blow mechanical shockwave generation device 1 (FIG. 1A and FIG. 1B) is in operating condition, the rear section 116 of shockwave guide head 115 is in contact with the free end 119 of the first shockwave transfer device 109 and the front section 117 of the shockwave guide wave 115 comes into bearing contact with a second toroidal damping device 120 which surrounds the base of shockwave guide rod 118, and which rests, on the one hand, on the bottom of front section 112 of eighth chamber 101 and, on the other, on the front face 117 of shockwave guide head 115. The protrusion distance of first shockwave transfer device 109 and the length of eighth chamber 101 are determined, amongst others, to match these requirements. When free end 119 of first shockwave transfer device 109 bears on second shockwave transfer device 114 located in eighth chamber 101, interface device 102 is slightly pushed towards rear section 97 of seventh chamber 90 and third helical spring 110 is slightly compressed. The length and diameter of shockwave guide rod 118 are generally dictated by the implementation conditions. The maximum efficiency of the shockwave is obtained when the weight of striking hammer 92 (FIG. 2C) is equal to the weight of second shockwave transfer device 114. Impedance adjustment can be performed, on the one hand, by acting on the diameter of shockwave guide head 115 (FIG. 2D) and, on the other, by acting, to the maximum possible extent, on the length of third piston 94, while taking into account the operating requirements.

When the gas pressure in second duct 30 (FIG. 1B) is less than nominal, the second calibrated spring 41 pushes back first piston 35 towards the rear section 38 of second chamber 36. Valve shank 31 penetrates into first bore 34 of the head of first piston 35, until valve shank 31 abuts on bore bottom and, therefore, supply valve head 32 is pushed back, thereby compressing first calibrated spring 33 and releasing the gas flow from gas micro-container 9. When gas pressure in second duct 30 (FIG. 1C) builds up again, first piston 35 is pushed in, thereby compressing second helical spring 41 until, whereas valve head 32 moves back to rest against the second sealing device of the first type 29 under the action of first calibrated spring 33, valve shank 31 will loose contact with the bottom of first bore 34. It should be noted that, as gas expansion is of adiabatic type, the expanded gas is colder than ambient temperature and its reheating causes an increase of its pressure, limited by an additional back motion of first piston 35, thereby compressing second calibrated spring 41 until it possibly comes into contact with piston stop 40. The gas injected into second duct 30 (FIG. 1B and FIG. 2A) flows into third duct 42 and, from there, into third chamber 43 and pushes back second piston 45 against stop on rear section 44 of third chamber 43, unless second piston is already in contact. The third sealing device of the second type 58 is then located inside third chamber 43, which allows gas flow into fourth duct 56, then into fifth duct 62, to reach fourth chamber 64 which then charges itself with high pressure gas, at a pressure, for example, comprised between fifteen and thirty bar. Valve head 67 is now pressed onto the first sealing device of the third type 74, by first helical spring 73, on the one hand, and by high gas pressure, on the other. When nominal pressure is reached in fourth chamber 64, the shockwave generation device is ready for operation.

Shockwave generation begins by operating of hinged lever 51 (FIG. 1C and FIG. 2B) which pushes in first pusher 49, which, in turn, pushes back second piston 45 into third chamber 43, and control rod 54 moves in translation in third chamber 43 until the third sealing device of the second type 58 penetrates into fourth duct 56 and blanks off this duct so that fourth chamber 64 is isolated from the high pressure gas supply. Then, as first pusher 49 continues to be pressed in, the free end 55 of control rod 54 penetrates into second bore 59 until it pushes in the free end 77 of second pusher 76, which, in turn, causes separation of valve head 67 from the first sealing device of the third type 74 and compression of the first helical spring 73. Gas then flows into sixth duct 75 and into fifth chamber 72 and violently pushes back third piston 94 (FIG. 1C and FIG. 2C) which was initially in pressed-in position in fifth bore 83, through the action of second helical spring 96. Striking hammer 92 is then driven at high speed into sixth chamber 84, thereby compressing second helical spring 96, and striking head 95 strikes strike anvil 105 (FIG. 1D and FIG. 2D) of interface device 102, which generates a shockwave which successively propagates itself in interface device body 103, then into first shockwave transfer device 109, and is then transmitted to rear section 116 of shockwave guide head 115 to further propagate itself in shockwave guide rod 118 and to the object to be disintegrated. At end of travel of third piston 94 in fifth bore 83, decompression zone 85 is gradually uncovered and the gas begins to escape into rear section 86 of sixth chamber 84 and is evacuated to the outside through check valve 88 (if any) and through seventh duct 87. The pressure downstream of the third sealing device of the second type 58 becomes essentially equal to atmospheric pressure. Second helical spring 96 then pushes back striking hammer 92 and third piston 94 into fifth bore 83. First helical spring 73 pushes back discharge valve 65 into the bottom of rear section 63 (FIG. 1B and FIG. 2B) of fourth chamber 64 and restores initial sealing by way of the first sealing device of the third type 74 when second pusher 76 can assume its initial position again by release of the action on hinged lever 51, which permits the displacement of second piston 45 towards the rear sections 44 of third chamber 43, under the effect of high gas pressure in third chamber 43. The displacement motion of second piston 45 causes the motion of control rod 54 until the third sealing device of the second type 58 escapes from fourth duct 56, which allows gas supply to fourth chamber 64. The pressure drop in third chamber 43 initiates the pressure drop in third and second duct 43 and 30, which initiates the previously described gas supply cycle.

In an improved embodiment of the invention, third chamber 43 (FIG. 2B) is interconnected to the outside by a second calibrated discharge valve 121, in order to avoid a possible overpressure associated with gas reheating after expansion, or a leakage at valve head 32 (FIG. 1A) and at the first sealing device of the first type 19.

The single-blow mechanical shockwave generation device 1 can be used for disintegration of urinary stones and can have a fourth chamber 64 whose volume is preferably comprised between one and three cubic centimeters, as well as a striking hammer of a weight of approximately ten grams.

In an improved embodiment of the invention, and for applications other than that concerning urinary stone destruction, it is necessary to generate successive shockwave trains. For this purpose, between hinged lever 51 and first pusher 49, a successive shockwave triggering device is inserted. This triggering device is activated by operation of lever 51. This initiates the generation of several successive shockwaves, for example, in a number and at a pace predetermined by successive operations of first pusher 49, without requiring the releasing of hinged lever 51.

The invention claimed is:

1. A shockwave generation apparatus for disintegrating an object, the apparatus comprising: a striking device; a shockwave generator; a shockwave transmitter; a gas storage device; a gas source; a gas expansion device; a sealing arrangement; and a control device; wherein in a first position, the sealing arrangement is arranged to couple the gas source to the gas storage device through the gas expansion device; wherein the control device is structured and arranged to move the sealing arrangement to a second position in which fluid communication between the gas expansion device and the gas storage device is prevented while coupling the gas storage device to the striking device; wherein, the striking device, when coupled to the gas storage device, is structured and arranged to contact the shockwave generator, which is structured and arranged to produce a shockwave directable to an object to be disintegrated through the shockwave transmitter; and return elements arranged to return the striking device and the control device to their respective initial positions.

2. The apparatus of claim 1, wherein the gas source comprises a cylinder, and the cylinder is connected by a first duct to the gas expansion device, composed of a pressure relief valve arranged to reduce the pressure of the gas from the cylinder to an operational pressure.

3. The apparatus of claim 2, wherein the apparatus further comprises a cradle that includes a front half and a rear half, the rear half comprising a sliding support device, and the front half comprising a calibrated receptacle and a perforation device; wherein the first duct connects the perforation device and the gas expansion device composed of an integrated expansion device; and wherein the cylinder is a micro-container and is held by the cradle.

4. The apparatus of claim 3, wherein the integrated expansion device comprises a first chamber coupled to the first duct, the pressure relief valve, a second chamber, and a second duct; wherein the second duct is connected to the first chamber and the second chamber; wherein the pressure relief valve includes a valve head slidingly disposed in the first chamber and biased by a first spring, a valve shank slidingly disposed in the second duct, and a first piston slidingly disposed in the second chamber and biased by a second spring; and wherein a free end of the valve shank is operatively connected to the first piston such that the first piston can push the valve shank.

5. The apparatus of claim 4, wherein the control device comprises a third duct connected to the second chamber and a third chamber, a fourth duct connected to the third chamber, a fifth duct connected to the fourth duct, a second piston including a seal and slidingly disposed in the third chamber and the fourth duct, and a push rod operatively connected between a hinged lever and the second piston; and wherein operation of the hinged lever moves the second piston such that the seal blocks fluid communication between the third chamber and the fourth duct upstream of the fifth duct.

6. The apparatus of claim 5, wherein the gas storage device comprises a fourth chamber and a gas storage valve; and a first bore connects the fourth duct and the fourth chamber; a second bore connects the fourth chamber and a fifth chamber; the fourth chamber is connected to the fifth duct; the gas storage valve is disposed in the fourth chamber and includes a hollow valve head and a tubular valve body; the tubular valve body is slidingly disposed in the second bore and constitutes a sixth duct that connects the fourth chamber and the fifth chamber; a gas storage spring biases the gas storage valve such that there is no fluid communication between the fourth chamber and the fifth chamber; and a gas storage push rod is slidingly disposed in the first bore, whereby one end of the gas storage push rod is operatively connected to the hollow valve head and another end of the gas storage push rod can be engaged by the second piston, such that movement of the second piston can move the hollow valve head and allow fluid communication between the fourth chamber and the fifth chamber.

7. The apparatus of claim 6, wherein the striking device comprises a striking hammer including a hammer piston, hammer body, and striking head; the hammer piston is slidingly disposed in a third bore connecting the fifth chamber and a sixth chamber; the third bore includes a decompression zone; the hammer body and striking head being disposed in the sixth chamber; a hammer spring biases the hammer piston into the third bore; and a seventh duct and a check valve connect the sixth chamber to the atmosphere.

8. The apparatus of claim 7, wherein the shockwave generator comprises an interface device and a transfer device; wherein the sixth chamber is connected to a fourth bore, the fourth bore is connected to a seventh chamber, the seventh chamber is connected to a fifth bore, and the fifth bore is connected to an eighth chamber; the interface device has an end disposed in the sixth chamber and crosses through the fourth bore; the transfer device has an end operatively connected to the interface device; and a generator spring biases another end of the transfer device into contact with a guide head.

9. The apparatus of claim 8, wherein the shockwave transmitter comprises the guide head and a guide rod; and wherein the guide head is disposed in the eighth chamber and the guide rod extends out of the eighth chamber and is designed and arranged for at least indirect contact with the object to be disintegrated.

10. The apparatus of claim 7, wherein the weight of the striking hammer is about 10 grams.

11. The apparatus of claim 6, wherein the fourth chamber is designed and arranged to accommodate an operational pressure of about 15 bar to about 30 bar.

12. The apparatus of claim 6, wherein the fourth chamber has a volume of about 1 cubic centimeter to about 3 cubic centimeters.

13. The apparatus of claim 1, wherein the gas source contains carbon dioxide.

14. The apparatus of claim 13, wherein the carbon dioxide in the gas source is at a pressure of about 70 bar to about 200 bar.

15. The apparatus of claim 1, wherein the striking device returns to its initial position due to spring force, and the control device returns to its initial position due to pressure in the gas expansion device.

16. The apparatus of claim 1, further comprising a successive triggering device whereby a single actuation of the control device initiates the generation of several successive shockwaves.

17. A method of producing a high amplitude wave which can be used to disintegrate an object, the method comprising: storing a gas at a storage pressure; expanding a portion of the gas such that it is at an operational pressure that is less than the storage pressure; accumulating a volume of the gas at the operational pressure; actuating a control device to temporarily prevent a further accumulation of the volume of gas while the accumulated volume of gas generates the wave.

18. The method of claim 17, wherein the gas is stored in a cylinder, the storage pressure is in the range of about 70 bar to about 200 bar, and the operational pressure is in the range of about 15 bar to about 30 bar.

* * * * *